US010261052B2

(12) United States Patent
Miki et al.

(10) Patent No.: US 10,261,052 B2
(45) Date of Patent: Apr. 16, 2019

(54) ANCHOR BOLT DIAGNOSING SYSTEM, METHOD OF THE SAME, AND PROGRAM OF THE SAME

(71) Applicant: NEC Corporation, Tokyo (JP)

(72) Inventors: Kiyokazu Miki, Tokyo (JP); Osamu Hoshuyama, Tokyo (JP)

(73) Assignee: NEC CORPORATION, Tokyo (JP)

( * ) Notice: Subject to any disclaimer, the term of this patent is extended or adjusted under 35 U.S.C. 154(b) by 90 days.

(21) Appl. No.: 15/129,817

(22) PCT Filed: Dec. 26, 2014

(86) PCT No.: PCT/JP2014/084616
§ 371 (c)(1),
(2) Date: Sep. 27, 2016

(87) PCT Pub. No.: WO2015/145914
PCT Pub. Date: Oct. 1, 2015

(65) Prior Publication Data
US 2017/0138908 A1    May 18, 2017

(30) Foreign Application Priority Data
Mar. 28, 2014 (JP) .................................. 2014-069330

(51) Int. Cl.
G01N 29/24 (2006.01)
G01N 29/04 (2006.01)
(Continued)

(52) U.S. Cl.
CPC .......... *G01N 29/045* (2013.01); *E02D 27/00* (2013.01); *E02D 33/00* (2013.01); *G01N 2291/0258* (2013.01); *G01N 2291/2691* (2013.01)

(58) Field of Classification Search
CPC ......... G01N 29/045; G01N 2291/0258; G01N 2291/2691; E02D 33/00; E02D 27/00
(Continued)

(56) References Cited

U.S. PATENT DOCUMENTS 4,062,227 A * 12/1977 Heyman ................ G01B 17/04
73/579
4,062,229 A * 12/1977 Godfrey ................ G01H 13/00
73/582
2005/0223804 A1  10/2005 Nakamura

FOREIGN PATENT DOCUMENTS

CN      102207404     * 10/2011
EP      1236996 A1     9/2002
(Continued)

OTHER PUBLICATIONS

"Application of Hammering Method to Quantitative Nondestructive Inspection of Concrete Surface Layer Defect" Transactions of Japan Society of Civil Engineers, No. 704, vol. 55, pp. 65-78 (May 2002).
(Continued)

Primary Examiner — Helen C Kwok
Assistant Examiner — Nashmiya S Fayyaz
(74) Attorney, Agent, or Firm — Wilmer Cutler Pickering Hale and Dorr LLP

(57) ABSTRACT

An anchor bolt diagnosing system includes a vibration sensing clip that clips an anchor bolt, and senses a vibration power of the anchor bolt, a blow sensing hammer that gives a blow to the anchor bolt clipped by the vibration sensing clip, and senses blow strength, and a diagnoser that obtains the vibration power and the blow strength output from the vibration sensing clip and the blow sensing hammer, and diagnoses soundness of the anchor bolt in accordance with whether a ratio of the vibration power to the blow strength is higher than a predetermined value.

11 Claims, 15 Drawing Sheets

(51) Int. Cl.
*E02D 27/00* (2006.01)
*E02D 33/00* (2006.01)

(58) Field of Classification Search
USPC .................................................. 73/579, 581
See application file for complete search history.

(56) References Cited

FOREIGN PATENT DOCUMENTS

| | | |
|---|---|---|
| EP | 1526365 A1 | 4/2005 |
| JP | S54-102188 A | 8/1979 |
| JP | 3560830 B2 * | 9/2004 |
| JP | 2004-325224 A | 11/2004 |
| JP | 2010-203810 A | 9/2010 |
| JP | 2010-271116 A | 12/2010 |
| JP | 2012-168022 A | 9/2012 |
| WO | WO-02/18927 A1 | 3/2002 |
| WO | WO-2004/011893 A1 | 2/2004 |
| WO | WO-2009/041139 A1 | 4/2009 |

OTHER PUBLICATIONS

International Search Report issued by the Japan Patent Office as International Searching Authority for International Application No. PCT/JP2014/084616 dated Mar. 17, 2015 (5 pages).

* cited by examiner

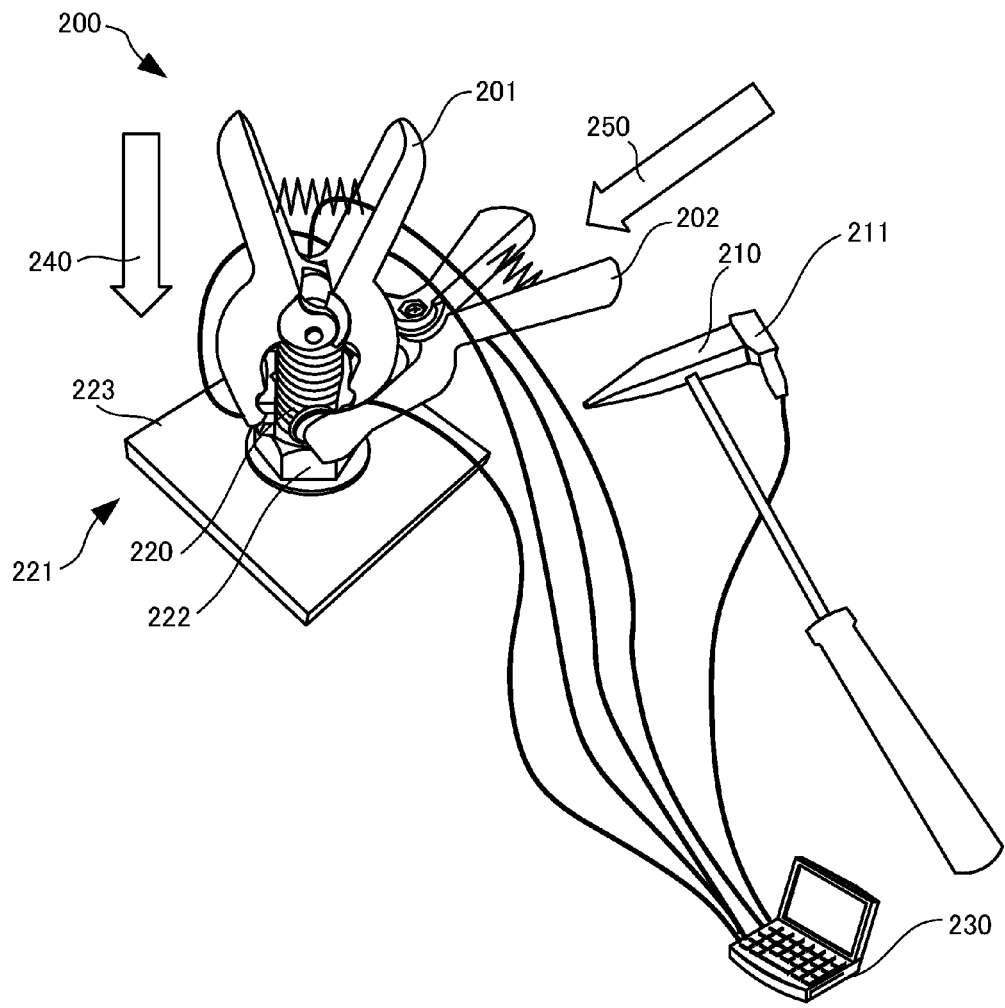
F I G. 2

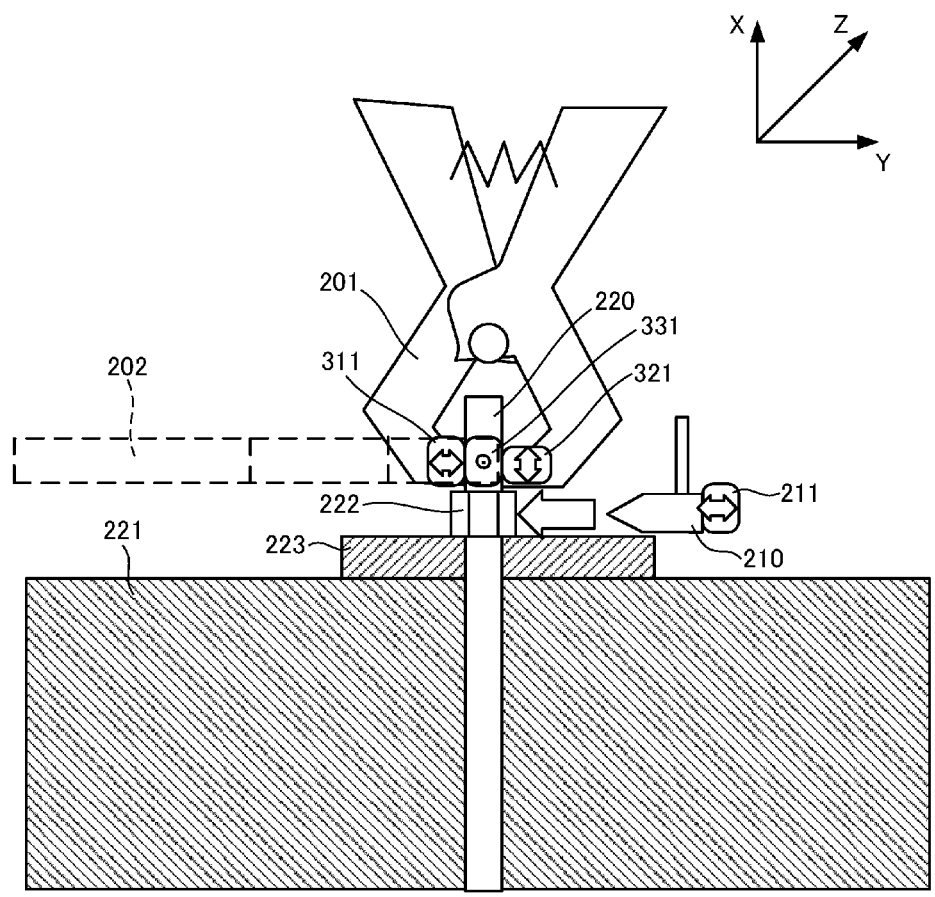
F I G. 4A

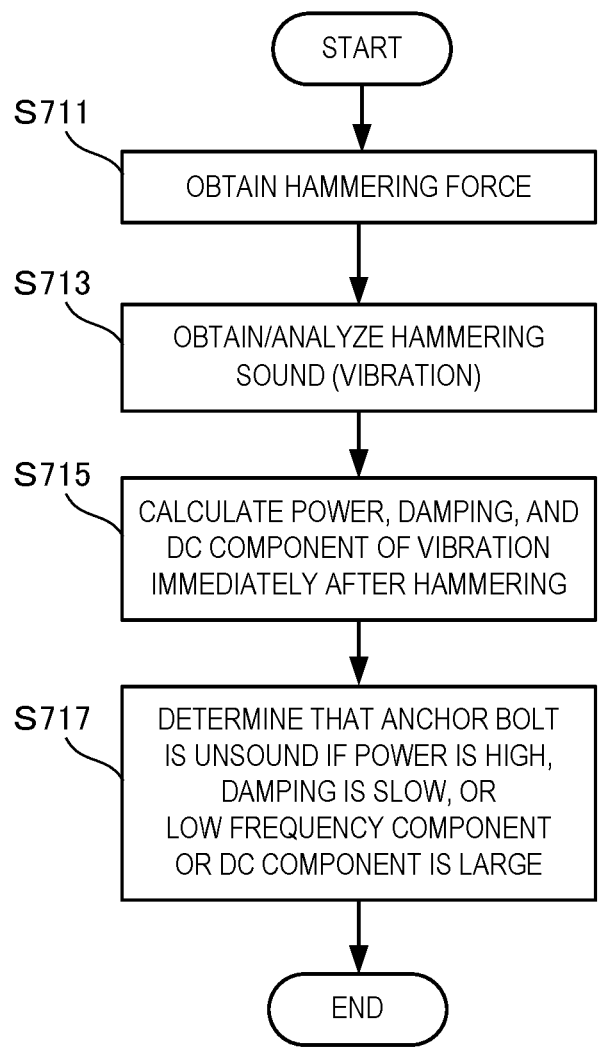
F I G. 7B

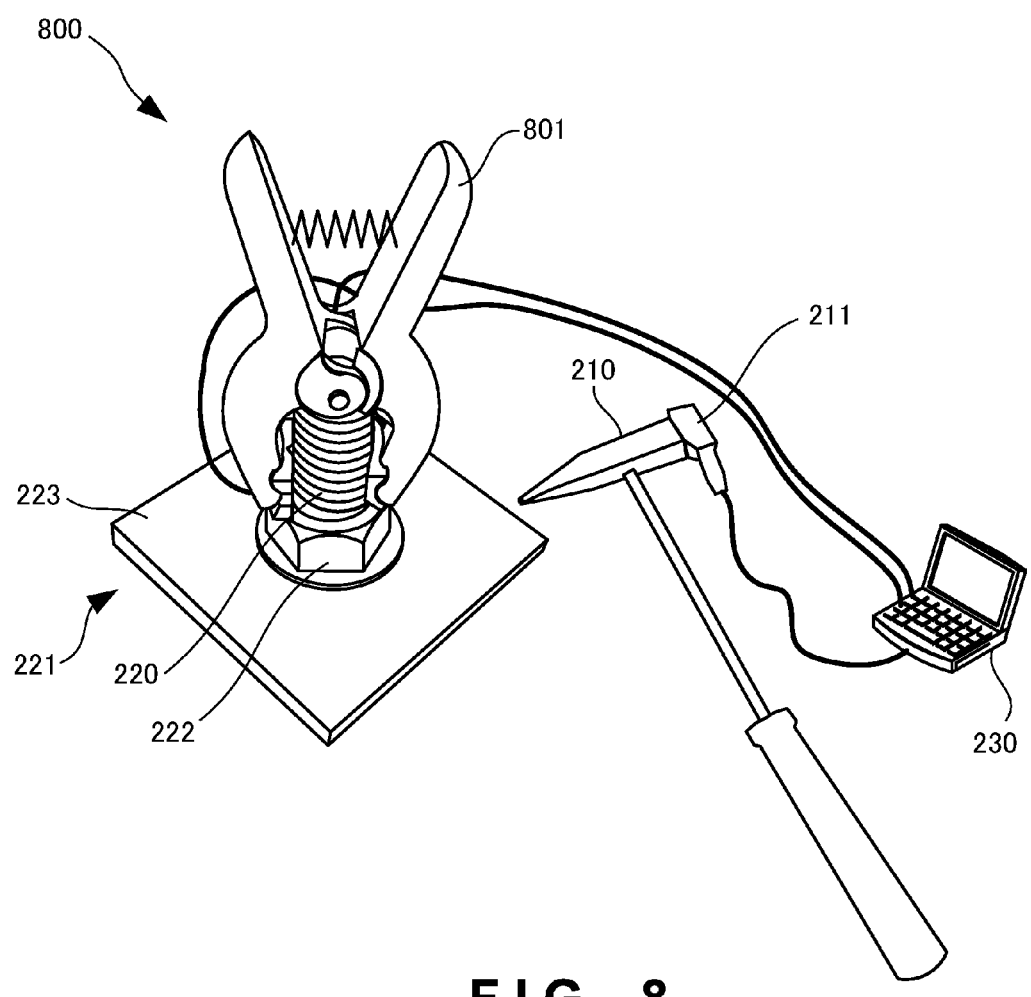
F I G. 8

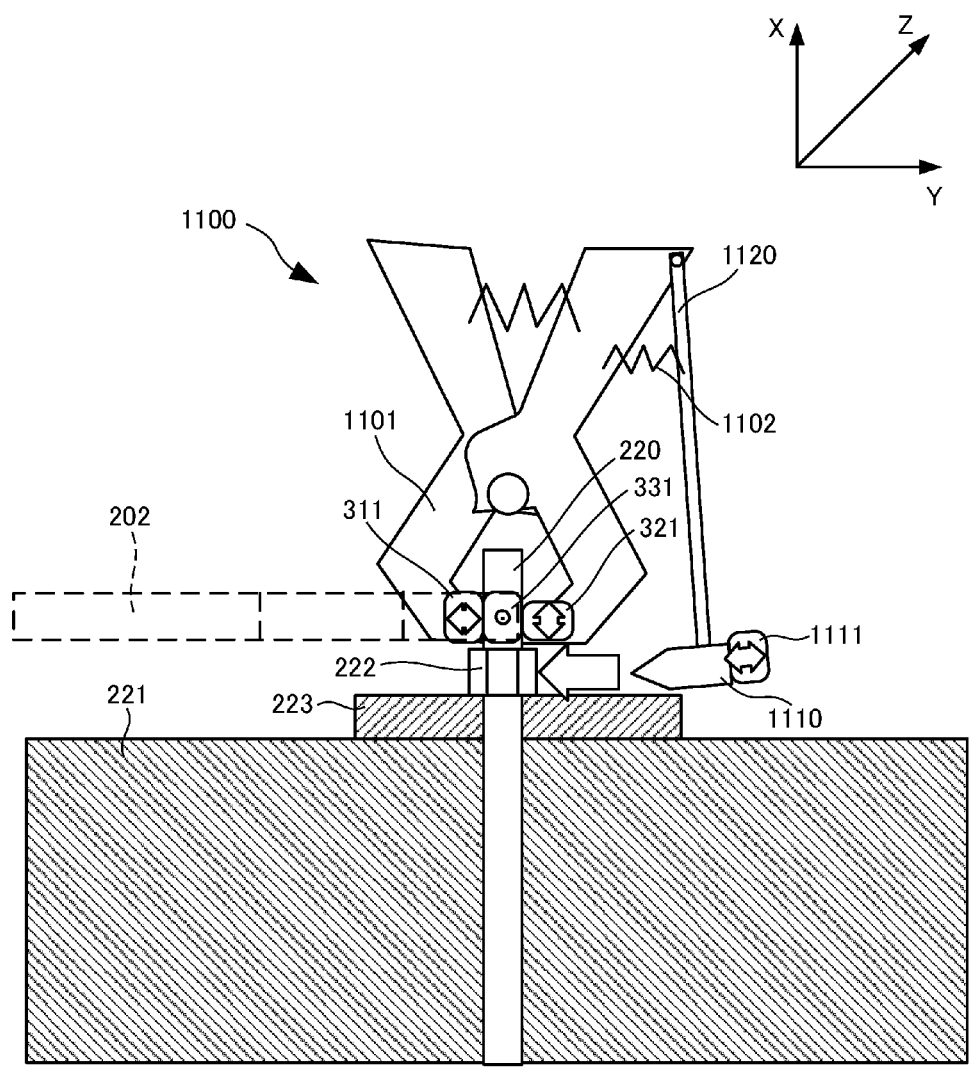
F I G. 11

ANCHOR BOLT DIAGNOSING SYSTEM, METHOD OF THE SAME, AND PROGRAM OF THE SAME

CROSS-REFERENCE TO RELATED APPLICATIONS

This application is a national stage application of International Application No. PCT/JP2014/084616 entitled "ANCHOR BOLT DIAGNOSING SYSTEM, METHOD OF THE SAME, AND PROGRAM OF THE SAME" filed on Dec. 26, 2014, which claims the benefit of the priority of Japanese Patent Application No. 2014-069330 filed on Mar. 28, 2014, the disclosures of each of which are hereby incorporated by reference in their entirety.

TECHNICAL FIELD

The present invention relates to an anchor bolt diagnosing system, a method of the same, and a program of the same.

BACKGROUND ART

In the above-mentioned technical field, patent literature 1 has disclosed a technique of diagnosing an anchor bolt by a natural vibration. Patent literature 2 has disclosed a technique which observes a physical property change surface by using the arrival time of a reflected wave as a clue. Non-patent literature 1 has disclosed a method of observing an amplitude by installing a vibration sensor on a concrete surface instead of an anchor bolt. Non-patent literature 2 has disclosed a technique which observes the amplitude of a hammering sound in order to check peeling of a concrete surface layer.

CITATION LIST

Patent Literature

Patent literature 1: Japanese Patent Laid-Open No. 2004-325224
Patent literature 2: Japanese Patent Laid-Open No. 2010-203810

Non-Patent Literature

Non-patent literature 1: Lecture Summaries of 2013 Autumn Lecture Meeting, November 2013, P33-36 "Experimental Study of Soundness Evaluation of Anchor Bolt Fixed Portion Based on Electromagnetic Pulse Method"
Non-patent literature 2: Transactions of Japan Society of Civil Engineers No. 704V55, 65-79, May 2002 "Application of Hammering Method to Quantitative Nondestructive Inspection of Concrete Surface Layer Defect"

SUMMARY OF THE INVENTION

Technical Problem

Unfortunately, these techniques described in the above-mentioned literatures cannot accurately diagnose the strength of an anchor bolt itself. This is so because the resonance of an incidental material (a material fixed by an anchor bolt) is dominant, so the anchor bolt is fixed by friction with the incidental material and does not sufficiently vibrate. Also, non-patent literatures 1 and 2 cannot diagnose the strength of an anchor bolt itself.

The present invention enables to provide a technique of solving the above-described problem.

Solution to Problem

One aspect of the present invention provides an anchor bolt diagnosing system comprising:
a vibration sensing clip that clips an anchor bolt, and senses a vibration power of the anchor bolt;
a blow sensing hammer that gives a blow to the anchor bolt clipped by the vibration sensing clip, and senses blow strength; and
a diagnoser that obtains the vibration power and the blow strength output from the vibration sensing clip and the blow sensing hammer, and diagnoses soundness of the anchor bolt in accordance with whether a ratio of the vibration power to the blow strength is higher than a predetermined value.

Another aspect of the present invention provides an anchor bolt diagnosing method comprising:
clipping an anchor bolt by a vibration sensing clip, and sensing a vibration power of the anchor bolt;
giving a blow to the anchor bolt clipped by the vibration sensing clip by using a blow sensing hammer, and sensing blow strength; and
obtaining the vibration power and the blow strength output from the vibration sensing clip and the blow sensing hammer, and diagnosing soundness of the anchor bolt in accordance with whether a ratio of the vibration power to the blow strength is higher than a predetermined value.

Still another aspect of the present invention provides an anchor bolt diagnosing program for causing a computer to execute:
clipping an anchor bolt by a vibration sensing clip, and sensing a vibration power of the anchor bolt;
giving a blow to the anchor bolt clipped by the vibration sensing clip by using a blow sensing hammer, and sensing blow strength; and
obtaining the vibration power and the blow strength output from the vibration sensing clip and the blow sensing hammer, and diagnosing soundness of the anchor bolt in accordance with whether a ratio of the vibration power to the blow strength is higher than a predetermined value.

Advantageous Effects of Invention

According to the present invention, it is possible to accurately, effectively, and efficiently diagnose the soundness of an anchor bolt.

BRIEF DESCRIPTION OF DRAWINGS

FIG. 2 is a view showing the configuration of an anchor bolt soundness diagnosing system according to the second embodiment of the present invention.

FIG. 4A is a view showing the configuration of the anchor bolt soundness diagnosing system according to the second embodiment of the present invention;

FIG. 7B is a flowchart for explaining the diagnosing method of the anchor bolt soundness diagnosing system according to the second embodiment of the present invention;

FIG. 8 is a view showing the configuration of an anchor bolt soundness diagnosing system according to the third embodiment of the present invention;

FIG. 11 is a view showing the configuration of an anchor bolt soundness diagnosing system according to the fourth embodiment of the present invention.

DESCRIPTION OF THE EMBODIMENTS

Preferred embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
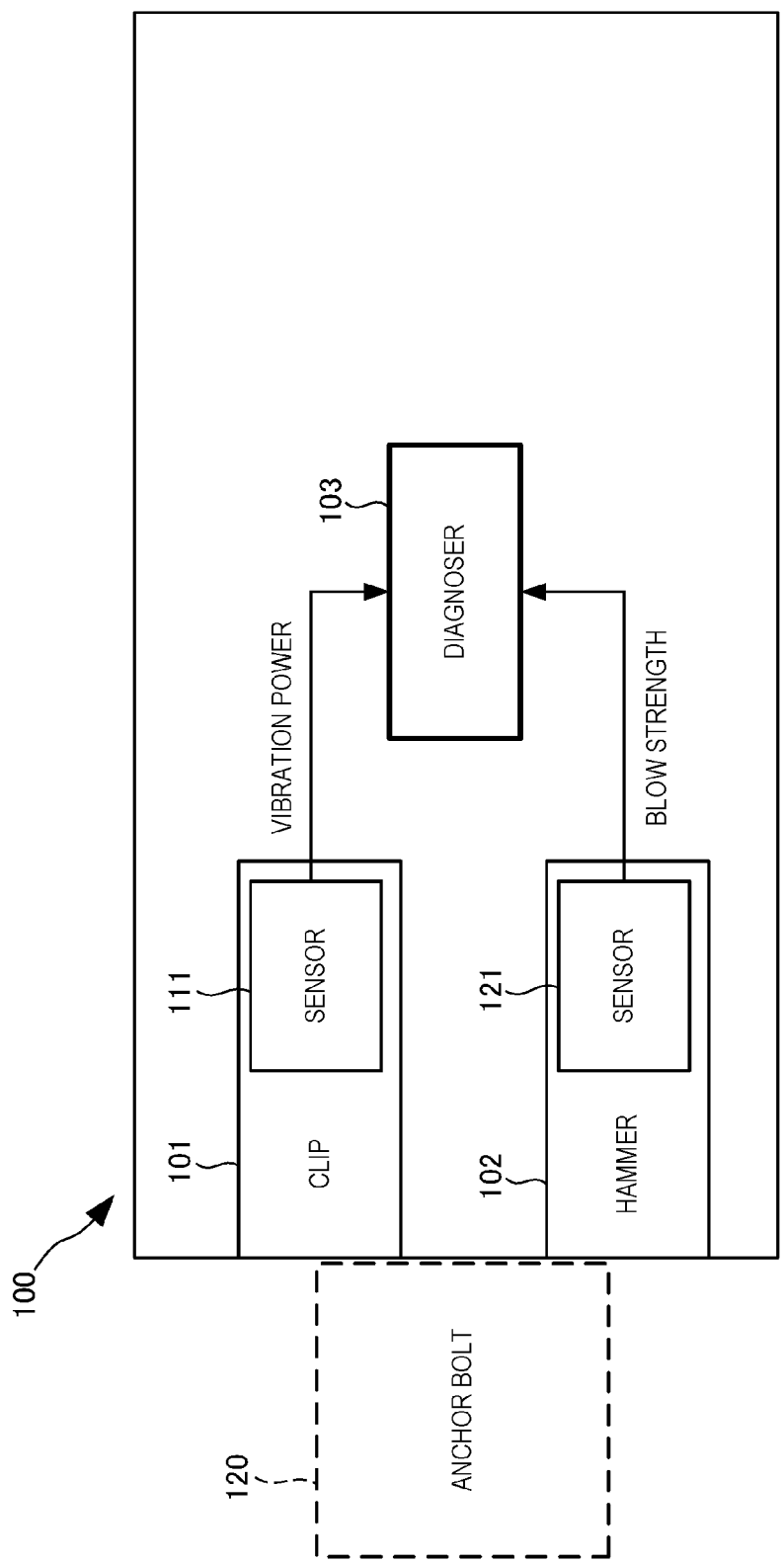
FIG. 1 is a block diagram showing the configuration of an anchor bolt soundness diagnosing system according to the first embodiment of the present invention.

An anchor bolt diagnosing system 100 as the first embodiment of the present invention will be explained with reference to FIG. 1. As shown in FIG. 1, the anchor bolt diagnosing system 100 includes a vibration sensing clip 101, a blow sensing hammer 102, and a diagnoser 103.

The vibration sensing clip 101 includes a sensor 111 which clips an anchor bolt 120 and senses the vibration power of the anchor bolt 120. The blow sensing hammer 102 gives a blow to the anchor bolt 120 clipped by the vibration sensing clip 101, and includes a sensor 121 for sensing the blow strength.

The diagnoser 103 obtains the vibration power and blow strength from the vibration sensing clip 101 and blow sensing hammer 102, and diagnoses the soundness of the anchor bolt 120 in accordance with whether the ratio of the vibration power to the blow strength is higher than a predetermined value.

The configuration as described above can accurately, effectively, and efficiently diagnose the soundness of an anchor bolt.

Second Embodiment

An anchor bolt diagnosing system 200 according to the second embodiment of the present invention will be explained below with reference to FIGS. 2 to 4. FIG. 2 is an outer appearance perspective view for explaining an outline of the configuration of the anchor bolt diagnosing system according to this embodiment.

As shown in FIG. 2, an anchor bolt 220 is driven into concrete 221, and an incidental material 223 is fixed to the concrete 221 by fastening a nut 222.

If the anchor bolt 220 as described above is not soundly driven into concrete, an accident such as removal or fall of the incidental material 223 occurs. Therefore, a method of accurately checking the soundness of an anchor bolt is necessary. Since, however, countless anchor bolts 220 are used in structures of the whole country, it is impossible to take a large working load and long working time to check the soundness of each anchor bolt, so high efficiency is required.

In this embodiment, therefore, the anchor bolt 220 is clipped by clips 201 and 202 with vibration sensors, and the nut 222 is hammered by a hammer 210 with an acceleration sensor 211. Diagnosis is performed by normalizing response vibrations in at least two directions by the hammering strength. The clip 201 clips the anchor bolt 220 in a direction (the direction of an arrow 240) from the distal end of the bolt in the axial direction to the concrete 221. On the other hand, the clip 202 clips the anchor bolt 220 in a direction (the direction of an arrow 250) perpendicular to the bolt axis. In this embodiment, the hammer 210 includes the acceleration sensor 211. However, the present invention is not limited to this, and a speed sensor may also be used.

A portion to be hammered by the hammer 210 is not limited to the nut 222, and may also be the anchor bolt 220 right above the nut 222. Hammering the root of the anchor bolt 220 as described above reduces influence which, e.g., the length of the anchor bolt 220 has on the response vibrations. The vibration sensors and the acceleration sensor 211 are connected to a diagnoser 230 such as a computer. The diagnoser 230 measures the hammering strength by the acceleration of the hammer 210, and compares a normalized hammering strength with a predetermined threshold, thereby diagnosing the soundness of fixing of the anchor bolt 220.

When performing measurement, the diagnoser 230 uses only an initial hammering response within a predetermined time after hammering, out of the obtained response vibrations. This can avoid the influences of the resonance and reverberation of the incidental material 223.

Since the clips are used, measurement can easily be performed in a site. It is important to bring the sensors into tight contact with a diagnosis target (e.g., an anchor bolt), and this can be implemented by softly fixing the vibration sensors to the clips 201 and 202 by using, e.g., a spring or soft material.

Also, in this embodiment, the diagnoser 230 displays an error message if the strength of hammering by the hammer 210 is low. The purpose of this error message is to cause a worker to strongly perform hammering to some extent, thereby obtaining an appropriate vibration response of an anchor bolt by overcoming friction of an incidental material.

Figure 3A:
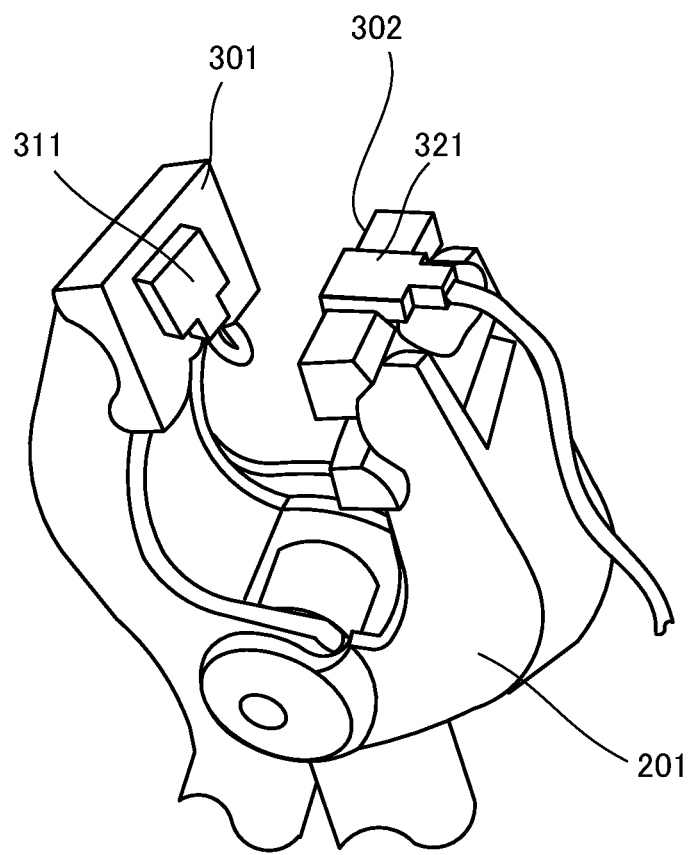
FIG. 3A is a view showing the arrangement of a clip according to the second embodiment of the present invention.

FIG. 3A is an enlarged view of the distal end portion (a surface which abuts against an anchor bolt) of the clip 201. A vibration sensor 311 for sensing vibrations in a direction perpendicular to the axis of the anchor bolt 220 is formed on an abutting surface 301 of the distal end portion of the clip 201, which abuts against the anchor bolt 220.

On the other hand, a vibration sensor 321 for sensing vibrations in the axial direction of the anchor bolt 220 is formed on an abutting surface 302 of the distal end portion of the clip 201, which abuts against the anchor bolt 220.

Figure 3B:
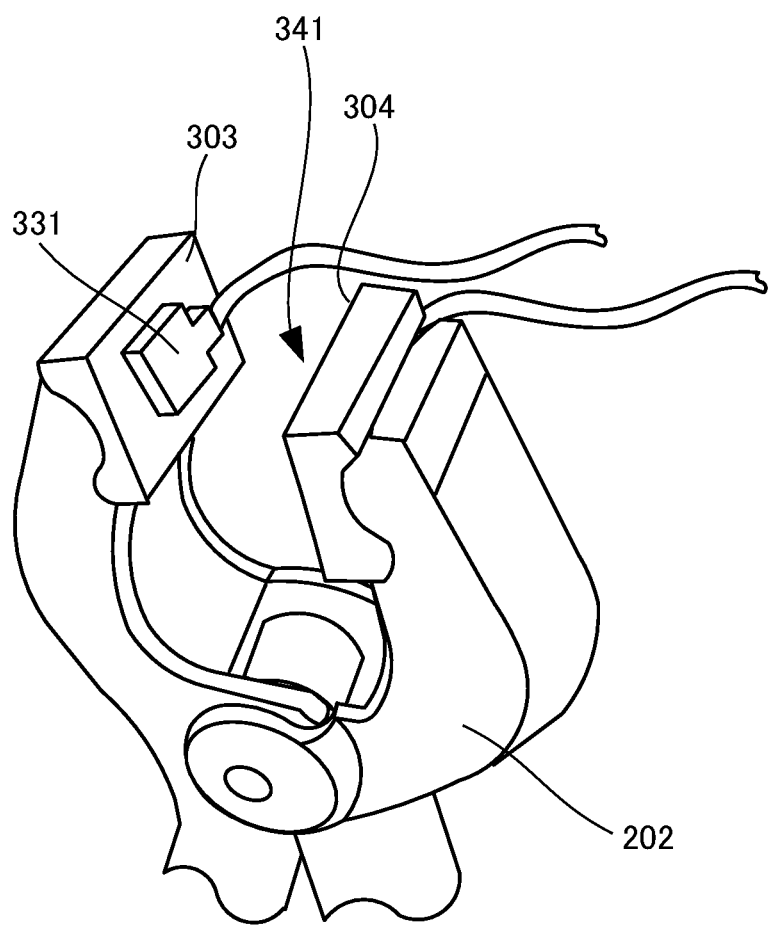
FIG. 3B is a view showing the arrangement of a clip according to the second embodiment of the present invention.

FIG. 3B is an enlarged view of the distal end portion (a surface which abuts against an anchor bolt) of the clip 202. A vibration sensor 3331 for sensing vibrations in the direction perpendicular to the axis of the anchor bolt 220 is formed on an abutting surface 303 of the distal end portion of the clip 202, which abuts against the anchor bolt 220.

On the other hand, a vibration sensor 341 for sensing vibrations in the axial direction of the anchor bolt 220 is formed on an abutting surface 304 of the distal end portion of the clip 202, which abuts against the anchor bolt 220.

FIG. 4A is a longitudinal sectional view schematically showing this system. For the sake of simplicity, cords extending from the sensors are omitted, and the clip 202 is made transparent. As shown in FIG. 4A, the vibration sensor 311 formed on the clip 201 is in tight contact with the anchor bolt 220, and senses vibrations in the Y direction. On the other hand, the vibration sensor 321 formed on the distal end of the other arm of the clip 201 is also in tight contact with the anchor bolt 220, and senses vibrations in the X direction.

In addition, the vibration sensor 331 formed on the clip 202 is in tight contact with the anchor bolt 220, and senses vibrations in the Z direction.

The acceleration sensor 211 is formed on the hammer 210, and senses the magnitude of impact applied to the nut 222. Thus, the connectivity between the concrete 221 and anchor bolt 220 and the soundness of the anchor bolt itself are diagnosed.

Figure 4B:
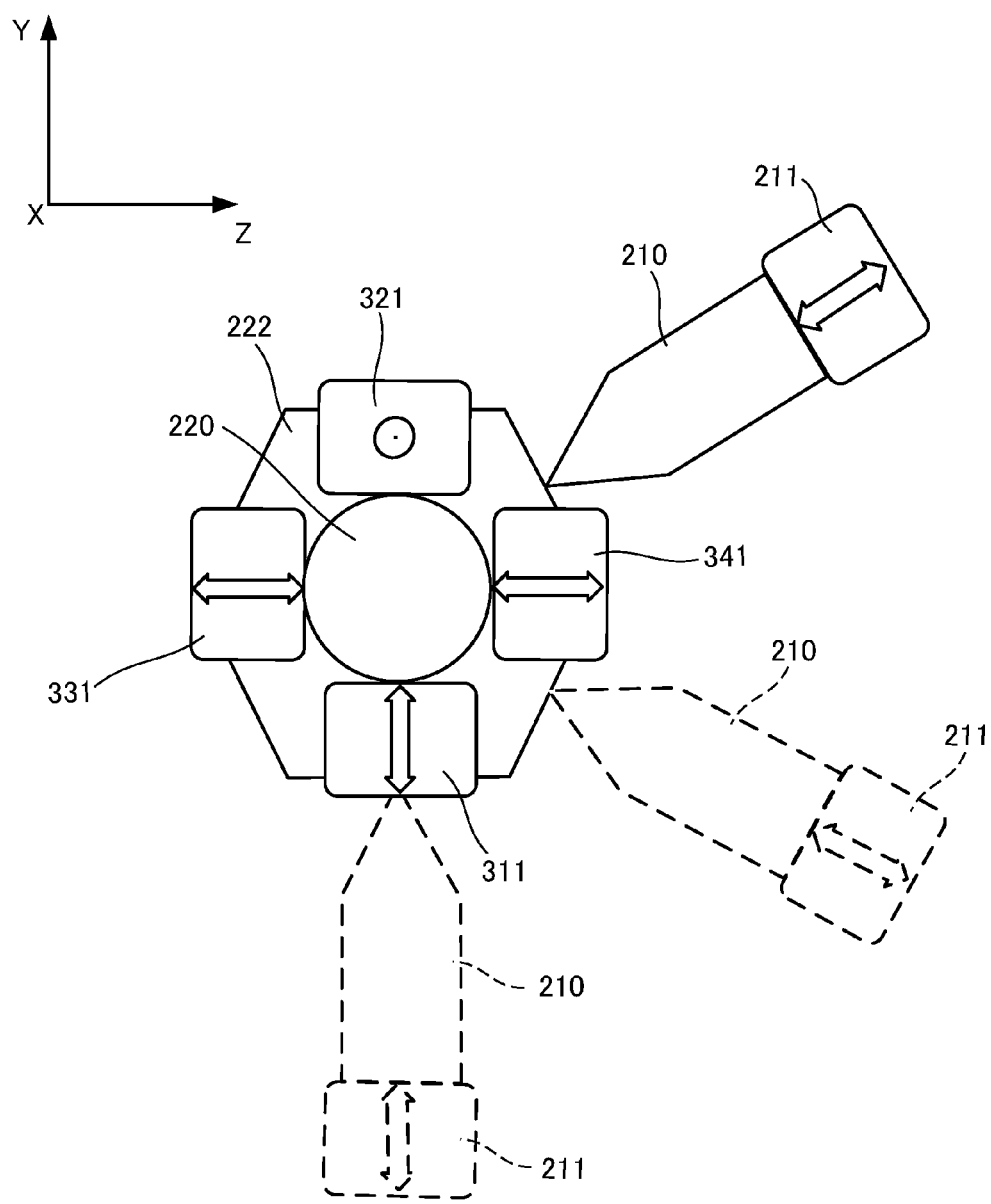
FIG. 4B is a view showing the configuration of the anchor bolt soundness diagnosing system according to the second embodiment of the present invention.

FIG. 4B is a cross-sectional view schematically showing this system. For the sake of simplicity, the clips are omitted, and only the sensors 311, 321, 331, and 341, anchor bolt 220, nut 222, and hammer 210 are shown.

As shown in FIG. 4B, the soundness of the anchor bolt is diagnosed by arranging the vibration sensors in the X, Y, and Z directions, and hammering the nut 222 with the hammer 210 in various directions. Hammering is desirably performed a number of times by the hammer 210 in different directions as shown in FIG. 4B, because the influence of the sensor attaching direction can be alleviated. Also, if deterioration has occurred, the direction of the deterioration can be sensed by performing hammering by changing the strength. A larger vibration response is obtained by hammering in the direction of deterioration. In addition, the relationship between the hammering strength and the vibration response (e.g., the presence/absence and degree of nonlinearity) can be checked by performing hammering by changing the strength. This makes it possible to know friction and mobility in more detail, and perform diagnosis with higher accuracy.

Furthermore, when hammering is performed a number of times, statistical processing of averaging the influence of friction which randomly varies whenever hammering is performed makes it possible to further increase the accuracy of the diagnostic result, and diagnose the soundness by using the frequency and magnitude themselves of the (frictional) variation as indices. When hammering is performed a number of times, it is also possible to use an accuracy increasing method which excludes an extremely deviated value (vibration response).

Figure 5:
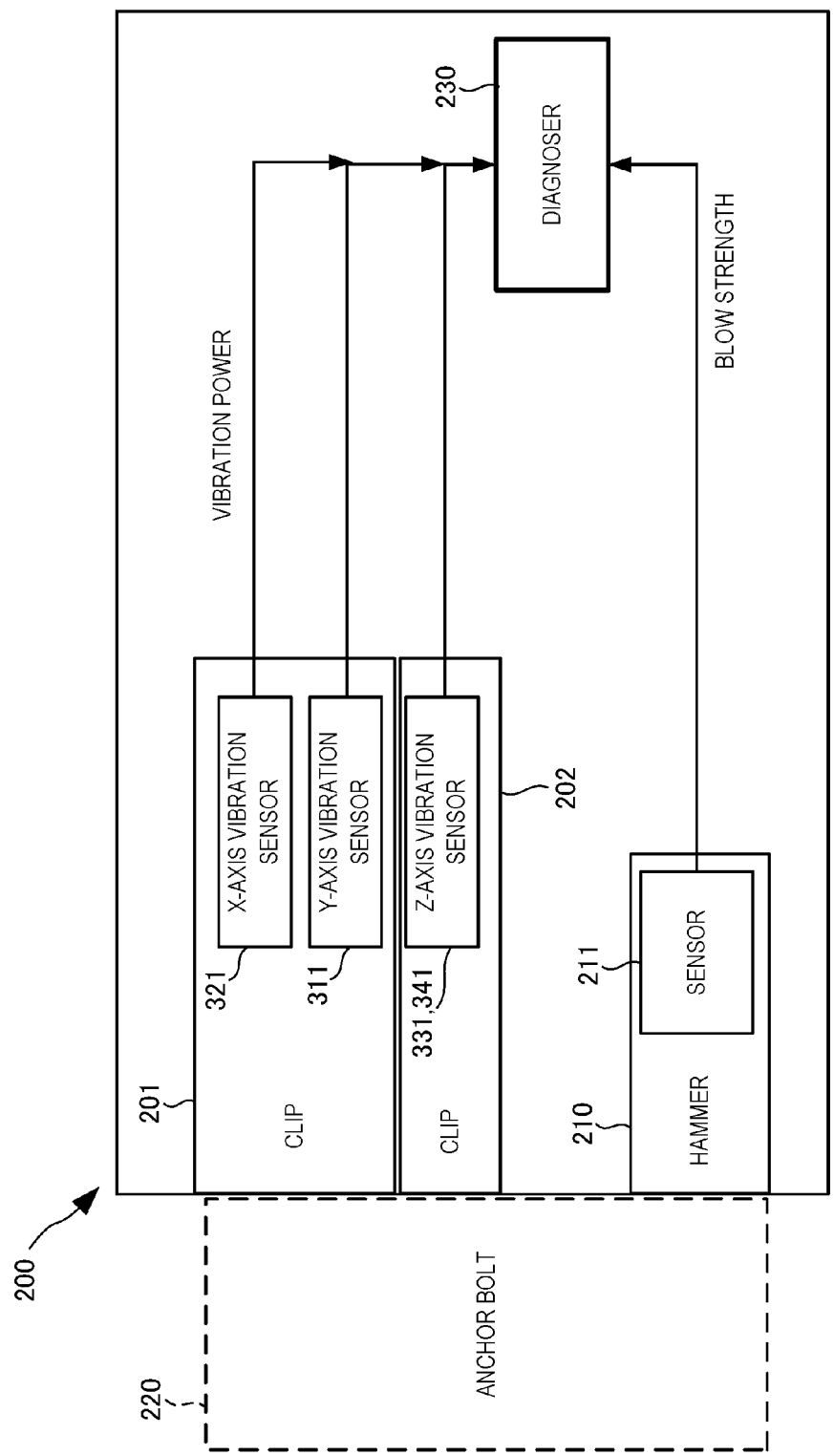
FIG. 5 is a block diagram showing the functional configuration of the anchor bolt soundness diagnosing system according to the second embodiment of the present invention.

FIG. 5 is a view showing the functional configuration of this system. As shown in FIG. 5, the anchor bolt diagnosing system 200 includes the clips 201 and 202, hammer 210, and diagnoser 230. The function of each element of this system will be explained again with reference to FIG. 5.

The clips 201 and 202 are vibration sensing clips which clip the anchor bolt 220, and sense the vibration powers of the anchor bolt 220 in at least two directions. The clips 201 and 202 include the vibration sensors 311, 321, 331, and 341 for sensing vibration powers in the axial direction (X-axis) of the anchor bolt 220 and the directions (Y- and Z-axes) perpendicular to the axis of the anchor bolt. Also, the hammer 210 is a blow sensing hammer which gives a blow to the anchor bolt 220 clipped by the clips 201 and 202, and senses the blow strength. The hammer 210 includes the sensor 211 as an acceleration sensor.

The diagnoser 230 obtains the blow strength and vibration power output from the clips 201 and 202 and the hammer, and diagnoses the soundness of the anchor bolt in accordance with whether the ratio of the vibration power to the blow strength is higher than a predetermined value. Also, the diagnoser 230 normalizes the response vibration obtained by the sensor 211 by the blow strength.

The diagnoser 230 diagnoses the soundness of the anchor bolt 220 by using the vibration power within a predetermined time after a blow is given to the anchor bolt 220 by the hammer 210. In particular, the diagnoser 230 diagnoses the soundness of the anchor bolt based on a low-frequency component of the vibration power. Furthermore, the diagnoser 230 diagnoses the soundness of the anchor bolt 220 when the blow strength to the anchor bolt 220 is equal to or larger than a predetermined value. The diagnoser 230 diagnoses the soundness of the anchor bolt 220 based on the blow strengths of a plurality of blows by the hammer 210 and the corresponding vibration powers sensed by the vibration sensors 311, 321, 331, and 341. In particular, the diagnoser 230 diagnoses the soundness of the anchor bolt 220 in accordance with the damping rates of the vibration powers sensed by the vibration sensors 311, 321, 331, and 341. If damping is slow, the diagnoser 230 determines that the soundness of the anchor bolt 220 is low.

The clips 201 and 202 include the vibration sensors 311, 321, 331, and 341 for obtaining the vibration power of the anchor bolt 220, on the surfaces which abut against the anchor bolt 220. The diagnoser 230 checks the power of only a part of an initial waveform of the hammering sound of the hammer 210. The degree of bend of the anchor bolt 220 is known from the vibration in the X-axis direction (bolt axial direction), and the soundness is known from the vibrations in the Y- and Z-axis directions (directions perpendicular to the bolt axis). Especially when the amounts of low-frequency components of the vibrations in the Y- and Z-axis directions (directions perpendicular to the bolt axis) are large, the diagnoser 230 can determine that the anchor bolt 220 is not firmly fixed.

Figure 6A:
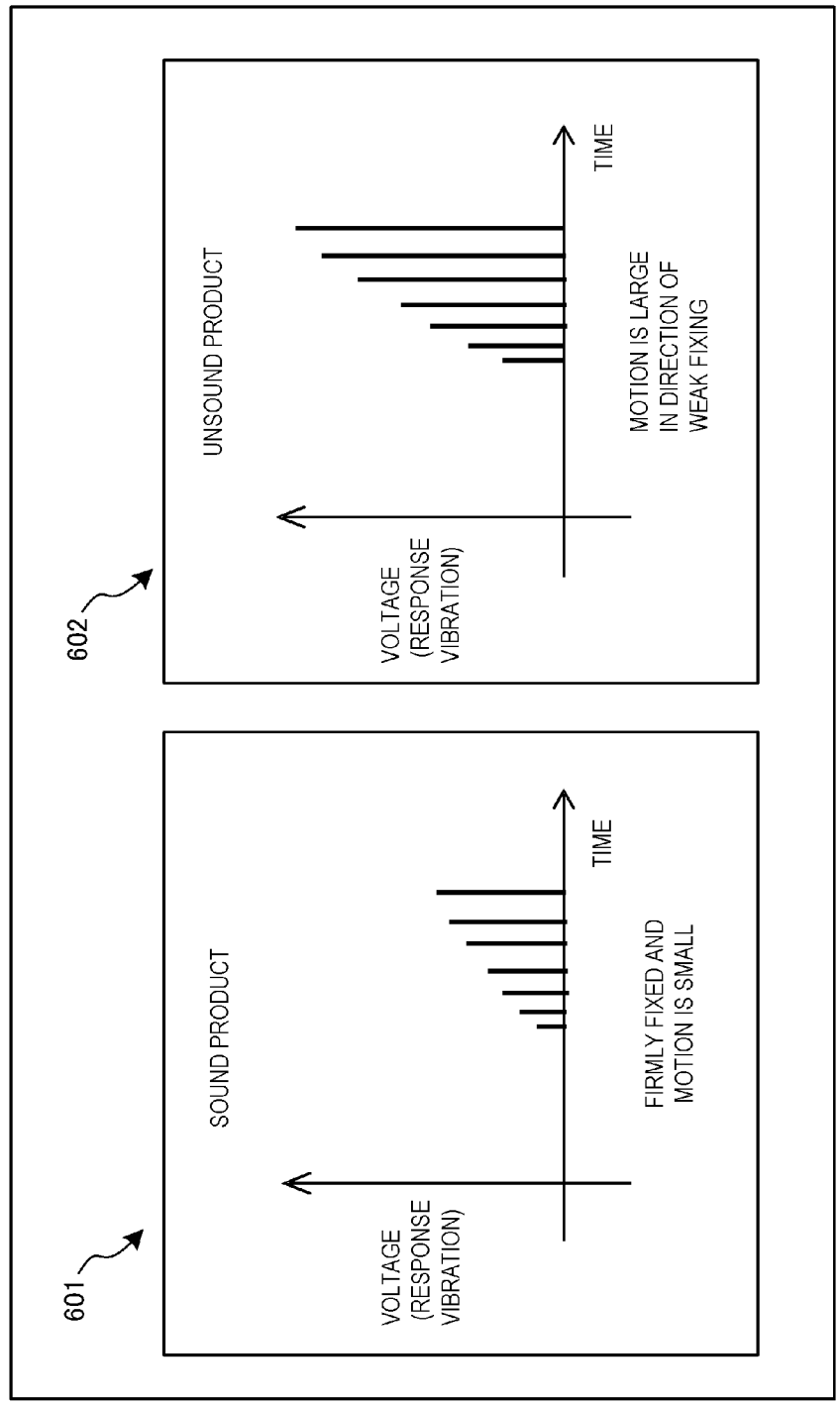
FIG. 6A is a view for explaining a diagnosing method of the anchor bolt soundness diagnosing system according to the second embodiment of the present invention.
Figure 6B:
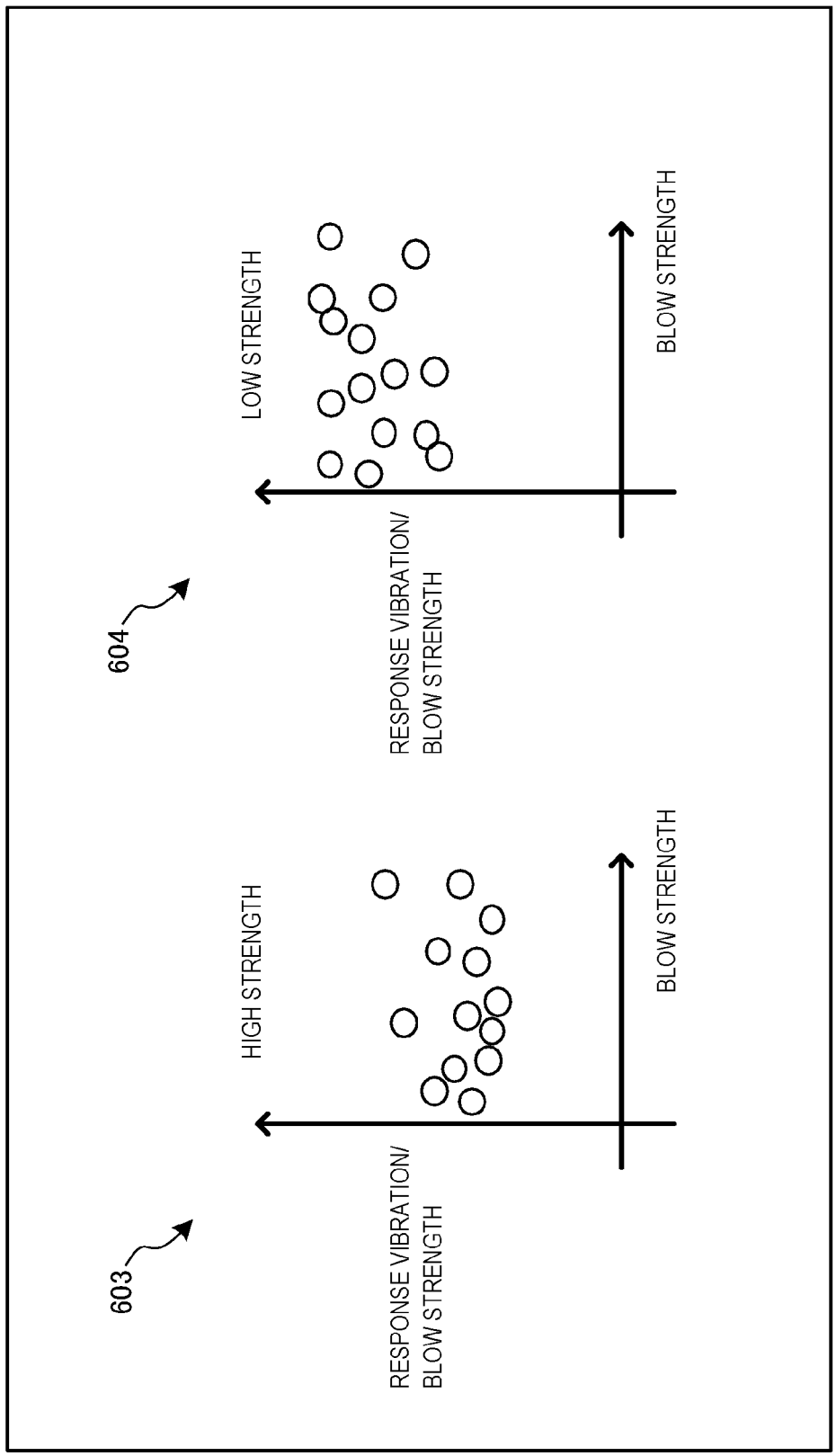
FIG. 6B is a view for explaining the diagnosing method of the anchor bolt soundness diagnosing system according to the second embodiment of the present invention.

As shown in FIG. 6A, the diagnoser 230 analyzes the height of a hammering waveform in a time domain. To avoid the influence of incidental material resonance, the second half of the waveform is not checked. Also, frequency analysis is performed to determine whether the Y- and Z-axes are DC-like, but the frequency analysis result is not used in soundness diagnosis. When the anchor bolt is sound, as shown in graph 601 in FIG. 6A, the vibration in the X-axis direction (bolt axial direction) immediately damps, and the vibrations in the Y- and Z-axis directions (directions perpendicular to the bolt axis) basically immediately damp. The vibrations in the Y- and Z-axis directions sometimes slowly damp because they resonate with a plate or the like. On the other hand, if the anchor bolt is unsound, as shown in graph 602 in FIG. 6A, the amplitude of the vibration in the X-axis direction is large, or damping is slow. In addition, as shown in graphs 603 and 604 in FIG. 6B, damping in the Y- and Z-axis directions is slow or becomes DC-like. On the other hand, the ratio of the response vibration to the blow strength increases as the strength decreases.

Hammering by the hammer 210 is preferably performed with a force stronger than friction of the incidental material.

Figure 7A:
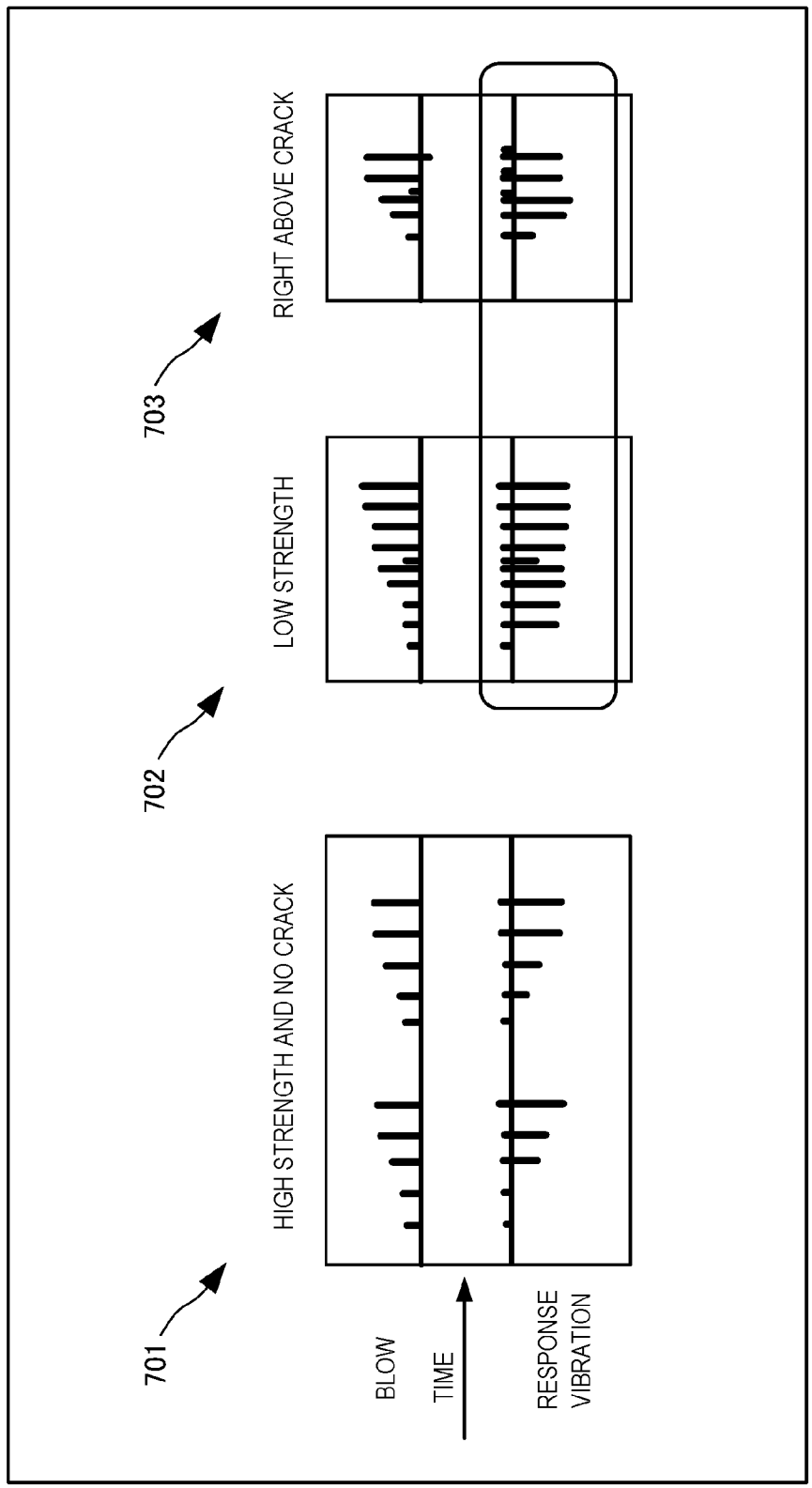
FIG. 7A is a view for explaining the diagnosing method of the anchor bolt soundness diagnosing system according to the second embodiment of the present invention.

As shown FIG. 7A, in a high-strength, no-crack case 701, the waveform of the response vibration is a tall triangle. However, the waveform of the response vibration is a trapezoid in a low-strength case 702 or right-above-crack case 703. The soundness of an anchor bolt can also be diagnosed by using these waveforms. The ratio of the peak height of the nut waveform to that of the hammer waveform can also be analyzed as a relationship with the hammer waveform peak height (blow strength). It is possible to determine that the strength is high when the ratio is low, and the strength is low when the ratio is high.

Note that the accuracy of diagnosis can be increased by using machine learning. It is also possible to identify soundness and unsoundness by using, e.g., an SVM (Support Vector Machine). Furthermore, the diagnostic result can also be normalized by the bolt diameter.

FIG. 7B is a flowchart for explaining the procedure performed by the diagnoser 230. The diagnoser 230 obtains a hammering sound from the hammer in step S711, obtains and analyzes a hammering sound in step S713, and obtains the vibration power immediately after hammering, the damping rate of the vibration, and the DC component of the vibration in step S715. In step S717, the diagnoser 230 determines the soundness of the anchor bolt by using the parameters obtained in step S715.

In this embodiment as has been explained above, it is possible to accurately, effectively, and efficiently diagnose the soundness of an anchor bolt by using the clips and hammer with the sensors.

Third Embodiment

An anchor bolt diagnosing system 800 according to the third embodiment of the present invention will be explained below with reference to FIG. 8. FIG. 8 is an outer appearance perspective view for explaining an outline of the configuration of the anchor bolt diagnosing system 800 according to this embodiment. The anchor bolt diagnosing system 800 according to this embodiment differs from the abovementioned second embodiment in that the system includes only one clip 801 and does not include the clip 202. The rest of the configuration and operations are the same as those of the second embodiment, so the same reference numerals denote the same parts and same operations, and a detailed explanation thereof will be omitted.

Figure 9:
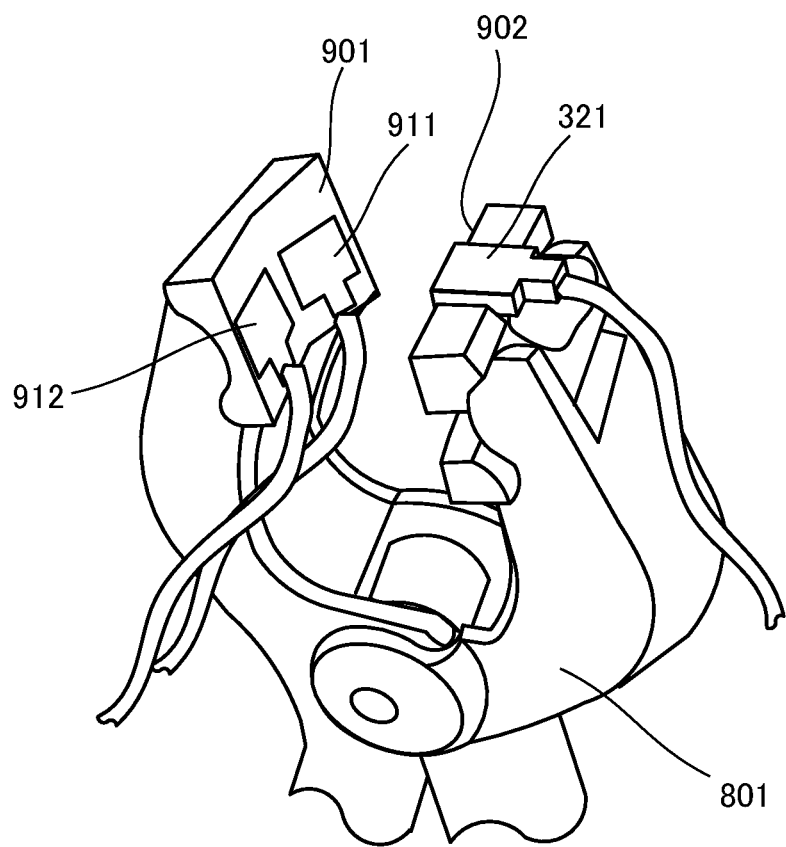
FIG. 9 is a view showing the arrangement of a clip according to the third embodiment of the present invention.

FIG. 9 is an enlarged view of the distal end portion (a surface which abuts against an anchor bolt) of the clip 801. Two vibration sensors 911 and 912 for sensing vibrations in directions perpendicular to the axis of an anchor bolt 220 are formed on an abutting surface 901 of the distal end portion of the clip 801, which abuts against the anchor bolt 220, and sense vibrations in different directions.

On the other hand, a vibration sensor 321 for sensing vibrations in the axial direction of the anchor bolt 220 is formed on an abutting surface 902 of the distal end portion of the clip 801, which abuts against the anchor bolt 220.

Figure 10:
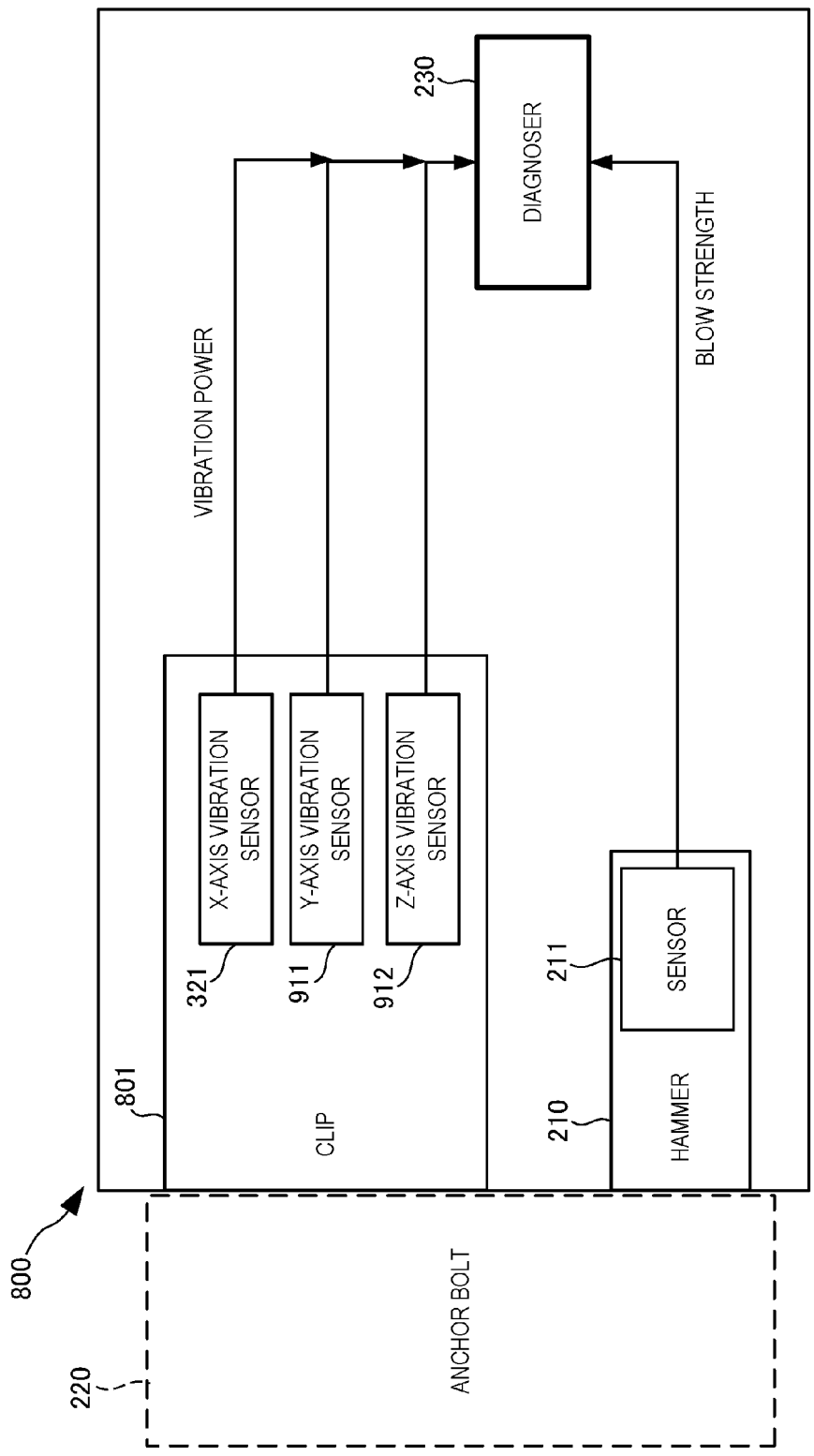
FIG. 10 is a block diagram showing the functional configuration of the anchor bolt soundness diagnosing system according to the third embodiment of the present invention.

FIG. 10 is a block diagram showing the functional configuration of this system. As shown in FIG. 10, the anchor bolt diagnosing system 800 includes the clip 801, a hammer 210, and a diagnoser 230. The clip 801 clips the anchor bolt 220, and senses the vibration powers of the anchor bolt 220 in at least two directions. The clip 801 includes the vibration sensors 321, 911, and 912 for sensing vibration powers in the axial direction (X-axis) of the anchor bolt 220, and the directions (Y- and Z-axes) perpendicular to the axis of the anchor bolt 220.

In this embodiment configured as described above, it is possible to diagnose the soundness of an anchor bolt more simply by using only one clip 801.

Fourth Embodiment

An anchor bolt diagnosing system 1100 according to the fourth embodiment of the present invention will be explained below with reference to FIG. 11. FIG. 11 is an outer appearance perspective view for explaining an outline of the configuration of the anchor bolt diagnosing system 1100 according to this embodiment. The anchor bolt diagnosing system 1100 according to this embodiment differs from the abovementioned second embodiment in that a hammer 1110 including an acceleration sensor 111 is connected to a clip 1101 and gives an impact to a nut 222 by a constant biasing force of a spring 1102. The rest of the configuration and operations are the same as those of the second embodiment, so the same reference numerals denote the same parts and same operations, and a detailed explanation thereof will be omitted.

In this embodiment, the strength of a blow to be given to an anchor bolt by the hammer can be made constant.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The present invention is applicable to a system including a plurality of devices or a single apparatus. The present invention is also applicable even when an information processing program for implementing the functions of the embodiments is supplied to the system or apparatus directly or from a remote site. Hence, the present invention also incorporates the program installed in a computer to implement the functions of the present invention by the computer, a medium storing the program, and a WWW (World Wide Web) server that causes a user to download the program. Especially, the present invention incorporates at least a non-transitory computer readable medium storing a program that causes a computer to execute processing steps included in the above-described embodiments.

This application claims the benefit of Japanese Patent Application No. 2014-069330 filed on Mar. 28, 2014, which is hereby incorporated by reference herein in its entirety.

The invention claimed is:

1. An anchor bolt diagnosing system comprising:
a vibration sensing clip that clips an anchor bolt, and senses a vibration power of the anchor bolt;
a blow sensing hammer that gives a blow to the anchor bolt clipped by said vibration sensing clip, and senses blow strength; and
a diagnoser that obtains the vibration power and the blow strength, and diagnoses soundness of the anchor bolt in accordance with whether a ratio of the vibration power to the blow strength is higher than a predetermined value,
wherein the vibration sensing clip includes:
a first vibration sensing clip including a vibration sensor connectable to a surface of a distal end portion of the anchor bolt, the first vibration sensing clip clipping the anchor bolt in an axial direction and a second vibration sensing clip including a vibration sensor connectable to the surface of the distal end portion of the anchor bolt, the second vibration sensing clip clipping the anchor bolt in a direction perpendicular to the axial direction.

2. An anchor bolt diagnosing system comprising:
a vibration sensing clip that clips an anchor bolt, and senses a vibration power of the anchor bolt;
a blow sensing hammer that gives a blow to the anchor bolt clipped by said vibration sensing clip, and senses blow strength; and
a diagnoser that obtains the vibration power and the blow strength and diagnoses soundness of the anchor bolt in accordance with whether a ratio of the vibration power to the blow strength is higher than a predetermined value,
wherein the vibration sensing clip includes:
   a first vibration sensing clip including a vibration sensor connectable to a surface of a distal end portion of the anchor bolt, the first vibration sensing clip clipping the anchor bolt in an axial direction and
   a second vibration sensing clip including a vibration sensor connectable to the surface of the distal end portion of the anchor bolt, the second vibration sensing clip clipping the anchor bolt in a direction perpendicular to the axial direction, and
   wherein one of the first vibration sensing clip and the second vibration sensing clip includes a vibration sensor for sensing vibrations in the axial direction of the anchor bolt and the other of the first vibration sensing clip and the second vibration sensing clip includes two vibration sensors for sensing vibrations in a direction perpendicular to the axial direction.

3. The anchor bolt diagnosing system according to claim 1, wherein said first vibration sensing clip senses vibration powers in the axial direction and said second vibration sensing clip senses vibration powers in the direction perpendicular to the axial direction.

4. The anchor bolt diagnosing system according to claim 1, wherein said diagnoser diagnoses the soundness of the anchor bolt based on a lower-frequency component of the vibration power.

5. The anchor bolt diagnosing system according to claim 1, wherein said diagnoser diagnoses the soundness of the anchor bolt when the blow strength with respect to the anchor bolt is not less than a predetermined value.

6. The anchor bolt diagnosing system according to claim 1, wherein said diagnoser diagnoses the soundness of the anchor bolt based on blow strengths of a plurality of blows given by said blow sensing hammer and corresponding vibration powers.

7. The anchor bolt diagnosing system according to claim 1, wherein said diagnoser diagnoses the soundness of the anchor bolt in accordance with a rate of damping of the vibration power.

8. The anchor bolt diagnosing system according to claim 1, wherein at least one of said first and second vibration sensing clips includes a vibration sensor that obtains the vibration power of the anchor bolt, on an abutting surface which abuts against the anchor bolt.

9. The anchor bolt diagnosing system according to claim 1, wherein said blow sensing hammer includes one of a speed sensor and an acceleration sensor, and normalizes a response vibration obtained by said acceleration sensor by the blow strength.

10. An anchor bolt diagnosing method comprising:
clipping an anchor bolt by a vibration sensing clip, and sensing a vibration power of the anchor bolt;
giving a blow to the anchor bolt clipped by the vibration sensing clip by using a blow sensing hammer, and sensing blow strength; and
obtaining the vibration power and the blow strength, and diagnosing soundness of the anchor bolt in accordance with whether a ratio of the vibration power to the blow strength is higher than a predetermined value,
wherein the vibration sensing clip includes:
   a first vibration sensing clip including a vibration sensor connectable to a surface of a distal end portion of the anchor bolt, the first vibration sensing clip clipping the anchor bolt in an axial direction and
   a second vibration sensing clip including a vibration sensor connectable to the surface of the distal end portion of the anchor bolt, the second vibration sensing clip clipping the anchor bolt in a direction perpendicular to the axial direction.

11. A non-transitory computer readable medium storing an anchor bolt diagnosing program for causing a computer to execute:
clipping an anchor bolt by a vibration sensing clip, and sensing a vibration power of the anchor bolt;
giving a blow to the anchor bolt clipped by the vibration sensing clip by using a blow sensing hammer, and sensing blow strength; and
obtaining the vibration power and the blow strength, and diagnosing soundness of the anchor bolt in accordance with whether a ratio of the vibration power to the blow strength is higher than a predetermined value,
wherein the vibration sensing clip includes:
   a first vibration sensing clip including a vibration sensor connectable to a surface of a distal end portion of the anchor bolt, the first vibration sensing clip clipping the anchor bolt in an axial direction and
   a second vibration sensing clip including a vibration sensor connectable to the surface of the distal end portion of the anchor bolt, the second vibration sensing clip clipping the anchor bolt in a direction perpendicular to the axial direction.

* * * * *